United States Patent [19]
Docoslis et al.

[11] Patent Number: 5,626,734
[45] Date of Patent: May 6, 1997

[54] FILTER FOR PERFUSION CULTURES OF ANIMAL CELLS AND THE LIKE

[75] Inventors: Aristides Docoslis, Buffalo; Nicolas Kalogerakis, Clarence, both of N.Y.; Leo A. Behie; Karan V. I. S. Kaler, both of Calgary, Canada

[73] Assignee: University Technologies International, Inc., Calgary, Canada

[21] Appl. No.: 516,698

[22] Filed: Aug. 18, 1995

[51] Int. Cl.$^6$ .................... C25B 1/00; C25B 7/00; G01N 27/26
[52] U.S. Cl. .................... 204/547; 204/565; 204/643
[58] Field of Search ................... 204/547, 565, 204/643

[56] References Cited

U.S. PATENT DOCUMENTS

| | | | |
|---|---|---|---|
| 4,326,934 | 4/1982 | Pohl | 204/180 |
| 4,441,972 | 4/1984 | Pohl | 204/180 |
| 4,956,065 | 9/1990 | Kaler et al. | 204/183.1 |
| 5,133,844 | 7/1992 | Stevens | 204/180.1 |
| 5,344,535 | 9/1994 | Betts et al. | 204/183.1 |
| 5,454,472 | 10/1995 | Benecke et al. | 209/127.1 |
| 5,489,506 | 2/1996 | Crane | 435/2 |

FOREIGN PATENT DOCUMENTS

| | | | |
|---|---|---|---|
| 136895 | 8/1979 | Germany | G01N 27/26 |
| 2238619 | 11/1990 | United Kingdom | G01N 27/26 |
| 2266153 | 4/1993 | United Kingdom | B01D 57/02 |
| 2266153 | 10/1993 | United Kingdom | B01D 57/02 |
| WO91/11262 | 8/1991 | WIPO | B03C 5/00 |
| 94/22583 | 10/1994 | WIPO . | |
| WO94/22583 | 10/1994 | WIPO | B03C 5/00 |

OTHER PUBLICATIONS

Fuhr et al. (Cell Manipulation and Cultivation under A.C. Electric Field Influence in Highly Conductive Culture Media, Biochimica et Biophysica Acta, 1201, 353–360) Dec. 15, 1994.

Markx et al. (Dielectrophoretic Separation of Cells: Continuous Separation, Biotechnology and Bioengineering, 45, 337–347) Feb. 20, 1995.

Spin Filter Perfusion System for High Density Cell Culture: Production of Recombinant Urinary Type Plasminogen Activator in CHO Cells, George C. Avgerinos, Denis Drapeau, Jeff S. Socolow, Jen–i Mao, Kathy Hsiao, and Robert J. Broeze, Bio/Technology, vol. 8, Jan., 1990, pp. 54–58.

Baculovirus Expression System Scaleup by Perfusion of High–Density Sf–9 Cell Cultures, Antoine W. Caron, Rosanne L. Tom, Amine A. Kamen, and Bernard Massie, Biotechnology and Bioengineering, vol. 43, pp. 881–891 (1994). No month available.

Vortex flow filtration of mammalian and insect cells, Steven J. Hawrylik, David J. Wasilko, Joann S. Pillar, John B. Cheng and S. Edward Lee, Cytotechnology 15: 253–258, 1994. No month available.

(List continued on next page.)

*Primary Examiner*—Kathryn L. Gorgos
*Assistant Examiner*—Alexander Noguerola
*Attorney, Agent, or Firm*—Anthony R. Lambert

[57] ABSTRACT

A filter has a conduit having an opening for flow of fluid into the conduit, a pump for pumping fluid into the conduit through the opening, electrodes spaced apart from each other across the opening such that fluid flowing through the opening passes between the electrodes; and an AC electrical source for the electrodes, the source of AC electrical energy having a frequency and voltage such that an electric field created by the AC electrical energy in the area around the electrodes imposes a negative dielectrophoretic force on target particles carried by the fluid, the negative dielectrophoretic force being opposed to the direction of fluid flow through the opening and having sufficient strength to prevent the target particles from passing between the electrodes into the conduit. The filter is mounted in a bioreactor for filtering viable cells and retaining them in culture medium.

24 Claims, 7 Drawing Sheets

OTHER PUBLICATIONS

High–Density Continuous Cultures of Hybridoma Cells in a Depth Filter Perfusion System, Duk Jae Oh, Sang Kyo Choi, and Ho Nam Chang, Biotechnology and Bioengineering, vol. 44, pp. 895–901 (1994) No month available.

Influence of the Screen Material on the Fouling of Spin Filters, Laurent R.J. Esclade, Stephane Carrel, and Paul Peringer, Biotechnology and Bioengineering, vol. 38, pp. 159–168 (1991). No month available.

Viable Cell Recycle with an Inclined Settler in the Perfusion Culture of Suspended Recombinant Chinese Hamster Ovary Cells, James A. Searles, Paul Todd, and Dhinakar S. Kompala, Biotechnol. Prog. 1994, 10, 198–206. No month available.

Enhanced antibody production associated with altered amino acid metabolism in a hybridoma high–density perfusion culture established by gravity separation, Henrik Albahn Hansen, Bo Damgaard and Claus Emborg, Cytotechnology II: 155–166, 1993. No month available.

Selective Recycle of Viable Animal Cells by Coupling of Airlift Reactor and Cell Settler, Manfred Hulscher, Uwe Scheibler, and Ulfert Onken, Biotechnology and Bioengineering, vol. 39, pp. 442–446 (1992) No month available.

Interaction of cell culture with downstream purification: a case study, Wolf Berthold and Ralph Kempken, Cytotechnology 15: 229–242, 1994. No month available.

Acoustic Cell Filter for High Density Perfusion Culture of Hybridoma Cells, Felix Trampler, Stefan A. Sonderhoff, Phylis W.S. Pui, Douglas G. Kilburn and James M. Piret, Bio/Technology vol. 12, Mar., 1994, pp. 281–284.

A Novel Ultrasonic Resonance Field Device for the Retention of Animal Cells, O. Doblhoff–Dier, Th. Gaida, and H. Katinger, Biotechnol. Prog., 1994, col. 10, No . 4, pp. 428–432. No month available.

Dielectrophoretic concentration of micro–organisms using grid electrodes, G.P. Archer, J.C. Render, W.B. Betts, and M. Sancho, Microbios 76: 237–244, 1993. No month available.

Electrode design for negative dielectrophoresis, Y. Huang and R. Pethig, Meas. Sci. Technol. 2 (1991), 1142–1146. No month available.

Electrokinetic behaviour of colloidal particles in travelling electric fields: studies using yeast cells, Y. Huang, X–B Wang, JA Tame and R. Pethig, J. Phys. D: Appl. Phys. 26: 1528–1535. No date available.

Positive and negative dielectrophoretic collection of colloidal particles using interdigitated castellated microelectrodes, Ronald Pethig, Ying Huang, Xiao–Bo Wang and Julian P.H. Burt, J. Phys. D. Appl. Phys. 24 (1992) 881–888. No month available.

Dielectrophoretic Separation of Cells: Continuous Separation, Gerard H. Markx and Ronald Pethig, Biotechnology and Bioengineering, vol. 45, pp. 337–343 (1995). No month available.

Dual–frequency dielectrophoretic levitation of Canola protoplasts, Karan V.I.S. Kaler, Jing–Ping Xie, Thomas B. Jones, and Reginald Paul, Biophysical Journal, vol. 63, Jul., 1992, pp. 58–69.

The primary stages of protein recovery, Shwu–Maan Lee, Journal of Biotechnology, II(1989) pp. 103–118. No month available.

Scale–Up and Validation of Sedimentation Centrifuges, Part I: Scale–up, J.T. Mahar, BioPharm, Sep. 1993, pp. 42–51.

Dielectrophoresis, The behaviour of neutral matter in non-uniform electric fields, Herbert A. Pohl, Cambridge University Press 1978, pp. 350–539. No month available.

Cell manipulation and cultivation under a.c. electric field influence in highly conductive culture media, Gunter Fuhr, Henning Glasser, Torsten Muller, Thomas Schnelle, Biochimica et Biophysica Acta 1201 (1994) 353–360, Mar. 21, 1994.

FILTER FOR PERFUSION CULTURES OF ANIMAL CELLS AND THE LIKE

FIELD OF THE INVENTION

This invention relates to devices and methods used to separate one material from another.

BACKGROUND OF THE INVENTION

High cell density perfusion cultures has become the method of choice in in vitro animal cell cultivation for the production of numerous therapeutic proteins such as HBAg (hepatitis B surface antigan), tPA (tissue plasminogen activator), etc. which are of great commercial value. The major advantage of perfusion compared with the other popular types of cell cultures (e.g. batch or fed-batch) is the much higher productivity per culture volume. This is owing to the very high cell densities (10-fold or higher) that can be achieved.

High cell densities can only be attained with the use of an efficient cell filtration device, located in the effluent stream of the bioreactor. The role of that device is to prevent the entrainment of the viable cells outside of the bioreactor during the replenishment of the spent culture medium with fresh medium. A successful cell filter should be able to fulfil as many as possible of the following requirements: (1) Minimal cell damage or effect on cell growth and productivity. (2) Selective retention of the viable cells only. Non-viable cells must be removed from the culture, since they lyse and release undesirable components into the culture environment. (3) High cell retention efficiency. (4) Uninterrupted operation for long periods of cultivation. (5) Low energy consumption. (6) Simplicity in operation and maintenance. (7) Scale-up capabilities for large scale production units. (8) Compact structure. (9) Cost effectiveness.

Existing Cell Filtration Devices

Most devices that are currently used are based on conventional filtration techniques, though there are other implementations. However, all of these are subject to severe limitations. The most popular of them are summarized below:

(a) Membrane-based filtration devices

These devices use a suitable membrane as a barrier for the separation of the cells from the medium. There are numerous devices under this category and they are different in operation and performance. Among them one can find: spin filters, cross-flow filters, vortex flow filters and depth filters. See for example Avgerinos, George C., Drapeau, D., Socolow, Jeff, Mao, Jen-i, Hsiao, Kathy, Broeze, Robert J., 1990, "Spin Filter perfusion system for high density cell culture: production of recombinant urinary type plasminogen activator in CHO cells", Bio/Technology 8: 54–58;

Caron, Antoine W., Tom, Rosanne L., Kamen, Amine A., Massie, Bernard, 1994, "Baculovirus expression system scaleup by perfusion of high-density Sf-9 cell cultures", Biotechnology and Bioengineering 43: 881–891;

Hawrylik, Steven J., Wasiko, David J., Pillar, Joanne S., Cheng, John B., Lee, Edward S., 1994, "Vortex flow filtration of mammalian and insect cells", Cytotechnology 15: 253–258;

Oh, Duk Jae, Choi, Sang Kyo, Chang, Ho Nam, 1994, "High-density continuous cultures of hybridoma cells in a depth filter perfusion system", Biotechnology and Bioengineering 44: 895–901.

All of these devices are used as external components of the culturing vessel with important ramifications in cell viability and overall simplicity of whole operation.

An important disadvantage of this type of filtration devices is the progressive fouling of the membrane which leads to a discontinuous operation. Therefore, there is a very limited capability to run perfusion cultures for extended periods (more than 1,000 hours of continuous operation) See for example Esclade, Laurent R. J., Carrel, Stepbane, Peringer, Paul 1991. "Influence of the screen material on the fouling of spin filters". Biotechnology and Bioengineering 38: 159–168. Another severe problem is the shear stresses that cells experience during the filtration, which has a negative effect on cell viability and the overall bioreactor productivity. Obviously, such devices cannot attain to any degree selective separation of viable cells.

(b) Gravity settlers

Gravity settlers are mounted externally, on the top of the bioreactor. See for example Searles, James A., Todd, Paul, Kompala, Dhinakar S. 1994. "Viable cell recycle with an inclined settler in the perfusion culture of suspended recombinant Chinese Hamster Ovary cells". Biotechnology Progress 10: 198–206.

Hansen, Henrik Albahn, Damgaard, Bo, Emborg, Claus 1993: "Enhanced antibody production associated with altered amino acid metabolism in a hybridoma high-density perfusion culture established by gravity separation". Cytotechnology 11: 155–166.

Hulscher, Manfred, Scheibler, Uwe, Onken, Ulfert 1991. "Selective recycle of viable animal cells by coupling of airlift reactor and cell settler". Biotechnology and Bioengineering 39: 442–446.

The operation of these devices is based on gravitational forces which make the cells settle back to the bioreactor. Vertical and inclined configurations of cell settlers have been reported. This method seems to provide a degree of selective separation. This is based on the differences in the size and density between the viable, that settle faster, and the non-viable cells, that shrink upon death. Nevertheless, the selectivity is very poor as it results in only about 5.8% higher viability inside the bioreactor than that in the effluent stream. In other words, the efficiency of selective separation of viable cells is marginal.

These gravity devices have several limitations: (i) the size of the filter is quite large compared to the bioreactor itself and (ii) very low flow rates are necessary for the operation of the filter. The first limitation means that cells have to stay out of the bioreactor for prolonged periods of time (almost 2 hours) which adversely affects both cell viability and bioreactor productivity. The second limitation implies that the final cell densities cannot be very high, since there is limited supply of nutrients. Finally, besides the above limitations, the scale-up capabilities of these devices are also questionable.

(c) Centrifuges

In centrifugation, the density difference between cells and liquid is amplified through the application of the centrifugal force which arises by rotating the suspension at high speeds (i.e. 5,000 g or higher).

Two types of centrifuges prevail: (i) the tubular bowl and (ii) the disk stack centrifuge. See for example Berthold, Wolf, Kempken, Ralph 1994. "Interaction of cell culture with downstream purification: a case study". Cytotechnology 15: 229–242.

The tubular centrifuges are not good for long-time operations, because of the precipitation that occurs on the inside walls. The precipitation gradually reduces the separation efficiency by decreasing the effective radius. See for example Lee, S-M. 1989. "The primary stages of protein recovery." Journal of Biotechnology 11: 103–118.

The disk stack centrifuges appear to be more efficient, however, both have severe limitations.

The main disadvantages of all types of centrifuges are the reduction of the separation efficiency in large scale operations and most importantly, the extensive cell damage due to the high shear stresses. See for example Mahar, J. T., 1993. "Scale-up and validation of sedimentation centrifuges. Part I: Scale-up" Biopharm (September) 42–51.

(d) Acoustic cell filter

One of the most interesting devices that has become very recently commercially available, involves the use of high frequency, ultrasonic resonance fields to transiently aggregate animal cells. The overall separation efficiency ranges from 92% to 99% for flow rates up to 3 L/h. See for example Trampler, Felix, Sonderhoff, Stefan A., Pui, Phylis W. S., Kilburn, Douglas G., Piret, James M. 1994. "Acoustic cell filter for high density perfusion culture of hybridoma cells". Bio Technology 12: 281–284.

The performance of this novel device has not yet been completely studied. However, some of the drawbacks that are associated with the operation of the acoustic filter are already known. The most important is the requirement of a very high power input per liter of culture medium perfused (a typical number cited is: 500 W/L), see for example, Doblhoff-Dier, O., Gaida, Th., Katinger, H. 1994. "A novel ultrasonic resonance field device for the retention of animal cells". Biotechnology Progress 10: 428–432.

Another problem that derives from the first one, is the need for dissipation (removal) of all the generated heat. As a result, the operation of the device becomes significantly complex as an air cooling system must be employed for that reason. In addition, the side-effects of the cell exposure to an ultrasonic field of standing waves are still unknown.

Nonetheless, the most important limitation of this device is its inability to selectively retain viable cells in the bioreactor. In particular, Trampler et al. have reported only a 3% higher retention of viable cells which can be considered at best as marginal.

The direct conclusion that can be drawn from the above review of the state-of-the-art is that there is still a lot of room for improvement and application of novel techniques to solve the problem. The inventors strongly believe that through the use of dielectrophoresis (DEP), they can achieve all the objectives described in the beginning.

Dielectrophoresis: Background Information

Dielectrophoresis (Pohl, 1951) refers to the interaction between a non-uniform electric field and a neutral, but polarizable, particle placed into it. The result of the interaction is particle motion. The force that makes this particle move is called the dielectrophoretic (DEP) force. It can be shown that the time averaged DEP force, $<F_{DEP}>$, is related to the size and electrical properties of the medium and the cell by the following relationship:

$$<F_{DEP}> = 2\pi r_c^3 \epsilon_M Re[K_e(\omega)] \nabla E_{rms}^2$$

where $r_c$ is the cell radius, $\epsilon_M$ is the real part of the electric permittivity of the surrounding medium, and $K_e(\omega)$ is a measure of the particle effective polarizability—often called the Clausius Mossotti factor—and is a strong function of frequency, $\omega$. $E_{rms}$ is the root mean squared value of the applied electric field intensity. Complete details on the theory of dielectrophoresis can be found in Pohl, H. A., 1978. "Dielectrophoresis: The behaviour of neutral matter in non-uniform electric fields", Cambridge University Press.

The applied electric field can be both direct or alternating. The use of the latter is preferable, since it is not associated with the electrophoretic effect which is undesirable in most cases. The use of the alternating field also allows the exploitation of the cell and suspending medium properties that are frequency related. This is particularly important when high electrical conductivity media are used which is always the case with animal cell cultures. In such cases application of an A.C. field can minimize the induced electric current and therefore, the Joule effect (heat generation) as well.

The non-uniformity of the field implies the existence of regions with high and low field intensity. Depending on the electrical properties of the cells and those of the suspending medium as well as the frequency of the applied electric field, the DEP force can be either positive or negative. Positive forces attract the cells to regions of high field intensity whereas negative forces push the cells towards regions of low field intensity. The latter is often referred to as negative dielectrophoresis.

REVIEW OF THE STATE-OF-THE-ART:
Dielectrophoresis-based cell separators

Starting from a completely different objective, electrical engineers have studied the effect of dielectrophoresis on biological systems, primarily microbial and plant cells suspended in distilled water or very low conductivity solutions. The research has been restricted to studies of the electrical properties of biological cells and other micro-particles (e.g. colloidal matter) and their behaviour under non-uniform electric fields. Therefore, although these methods were concerned with cell separation and differentiation, the pieces of apparatus that were used can by no means be considered as integrated filtration devices.

Although many ideas have been proposed in

Archer, G. P., Render M. C., Betts, W. B., Sancho, M., 1993: "Dielectrophoetic concentration of microorganisms using grid electrodes". Microbios 76: 237–244., Huang, Y., Petbig, R., 1991. "Electrode design for negative dielectrophoresis". Meas. Sci. Technol. 2: 1142–114., Huang, Y, Wang X-B, Tame, J. A., Pethig, R., 1993. "Electrokinetic behaviour of colloidal particles in travelling electric fields: studies using yeast cells". J. Phys. D: Appl. Phys. 26: 1528–1535., Pethig, R., Huang, Y., Wang, Xiao-Bo, Burt, J. P. H., 1991. "Positive and negative dielectrophoretic collection of colloidal particles using interdigitated castellated microelectrodes". J. Phys. D: Appl. Phys. 24: 881–888, there has been only one device, so far as the inventors are aware, the operation of which was proven capable of providing continuous cell separation from a cell suspension in Markx, G. H., Pethig, R., 1994. "Dielectrophoretic separation of cells: continuous separation". Biotechnology and Bioengineering 45: 337–343.

This device has only been tested in a small scale operation but the cell separation efficiencies reported are very high. The selective separation between viable and nonviable cells is also significant (almost 100% in some cases). That became possible due to the electrode configuration that was used. The electrode shape and arrangement was such that it allowed viable cells, that were experiencing positive DEP, and nonviable cells, that were experiencing negative DEP, to be collected on different sides of the separation chamber. This separation became possible with the sequential operation of a set of pumps that were intermittently either injecting suspension into the chamber or moving the cell suspensions towards different exits of the chamber.

The above mentioned device is subject to severe limitations. First of all the suggested type of separation becomes possible if and only if the electrical conductivity of the medium is significantly lower than that of the viable cell cytoplasm. On the contrary, the actual culture medium contains high concentration of salts and hence, it has a conductivity much higher than that of the cells. Thus, in order for the separation to become feasible, a resuspension of the cells into a low conductivity medium is required. This means either an extra separation (with unacceptable increase in the risk of contaminating the culture) prior to the aforementioned one, or an extensive dilution of the original culture medium. The latter results in large liquid volumes that cannot be processed easily and efficiently and most importantly in a detrimental increment of the purification cost, if the main bioproduct is dissolved into the medium (e.g. monoclonal antibodies). Another disadvantage of this process is the extended residence time of the cells out of their growth environment. This period can be as long as 2 hours and places an unacceptable stress on the cell culture. In addition to that, a 2 hour continuous exposure of the cells in an electric field may be detrimental.

Therefore, extension of the above separation technique to perfusion cultures of animal cells will not work satisfactorily. Based on the previous discussion, it is apparent that this device is suitable only as a downstream purification step wherever the main product of the fermentation is the biomass itself (e.g. yeast cells).

SUMMARY OF THE INVENTION

All of the above mentioned limitations can be overcome with the proposed DEP-filter. Negative dielectrophoresis is a key ingredient for the successful removal of nonviable cells or other unwanted particles and high retention of viable cells or other target particles. The proposed device makes use of the DEP effect in a very suitable and efficient way. The idea of particle separation using negative DEP is based upon the potential of exploiting the difference in the electrical properties between a target particle, and an unwanted particle. This fact allows the manipulation of the separation conditions, so that cell selectivity in the separation can also be achieved (e.g. viable cells from debris, and also, it is reasonably believed, different cell types can be separated from each other). At the same time, the idea can be realized with very simple and practical means.

In general, the filter has application to filtration of any particle carried by a fluid, where the particle can be made to experience dielectrophoresis, and in particular where an unwanted particle is not significantly affected by dielectrophoresis.

There is therefore proposed in accordance with one aspect of the invention, a filter comprising a conduit having an opening for flow of fluid into the conduit, a pump for pumping fluid into the conduit through the opening, and means for producing a negative dielectrophoretic force on target particles carried by the fluid, the negative dielectrophoretic force being opposed to the flow of fluid and having sufficient strength to prevent the target particles from passing into the conduit.

Preferably, the dielectrophoretic force is created by electrodes spaced apart from each other across the opening such that fluid flowing through the opening passes between the electrodes; and a source of electrical energy for the electrodes, the source of electrical energy having a frequency and voltage such that an electric field created by the electrical energy between the electrodes imposes a negative dielectrophoretic force on target particles carried by the fluid, the negative dielectrophoretic force being opposed to the direction of fluid flow through the opening and having sufficient strength to prevent the target particles from passing between the electrodes into the conduit.

In accordance with a further aspect of the invention, there are plural pairs of parallel interdigitated electrodes extending across the opening.

The filter has particular applicability as a filter for a culture medium, and for that purpose may be mounted in a bioreactor, with the filter immersed in culture medium. In such a case, the target particles are viable cells and the medium will likely include unwanted cell debris that are substantially unaffected by the dielectrophoretic force such that the flow of fluid generated by the pump carries them into the conduit.

For separation of viable and non-viable cells, the source of electrical energy preferably has a frequency in the vicinity of 10 MHz or higher, namely at a level such that the unwanted particles, typically dead cells and cell debris, are substantially unaffected by the negative dielectrophoretic force.

In accordance with a further aspect of the invention, the conduit is oriented in a bioreactor such that flow of fluid in the bioreactor includes a component of flow parallel to the opening.

In accordance with a further aspect of the invention, there is provided a method for filtering target particles from a fluid, the method comprising the steps of:

pumping fluid into a conduit through an opening in the conduit; and applying a negative dielectrophoretic force on target particles at the opening, the negative dielectrophoretic force having sufficient strength to prevent the target particles from entering the conduit.

In accordance with a further aspect of the invention, the conduit is oriented such that direction of fluid flow into the conduit is opposed to the pull of gravity.

According to one aspect of the invention, the filter presented here is the first that is used as an internal part of the bioreactor, capable of providing cell separation without modification of the culture medium.

The primary function of the filter in a bioreactor is to retain viable cells in the bioreactor. The filter is not used for handling both viable and non-viable cells in different ways and then separate them by moving them towards different directions (as in recently published external cell separation device for yeasts). Here, the DEP repulsive forces (negative dielectrophoresis) introduced by the filter are against the drag forces acting on the cells by the effluent stream of the culture medium. Since the DEP forces are larger in magnitude for the viable cells, these cells are retained inside the bioreactor. The same is not true for the nonviable cells as they follow the spent medium in the effluent stream.

BRIEF DESCRIPTION OF THE DRAWINGS

There will now be described preferred embodiments of the invention, with reference to the drawings, by way of illustration, in which like numerals denote like elements and in which.

DETAILED DESCRIPTION OF PREFERRED EMBODIMENTS

Figure 1:
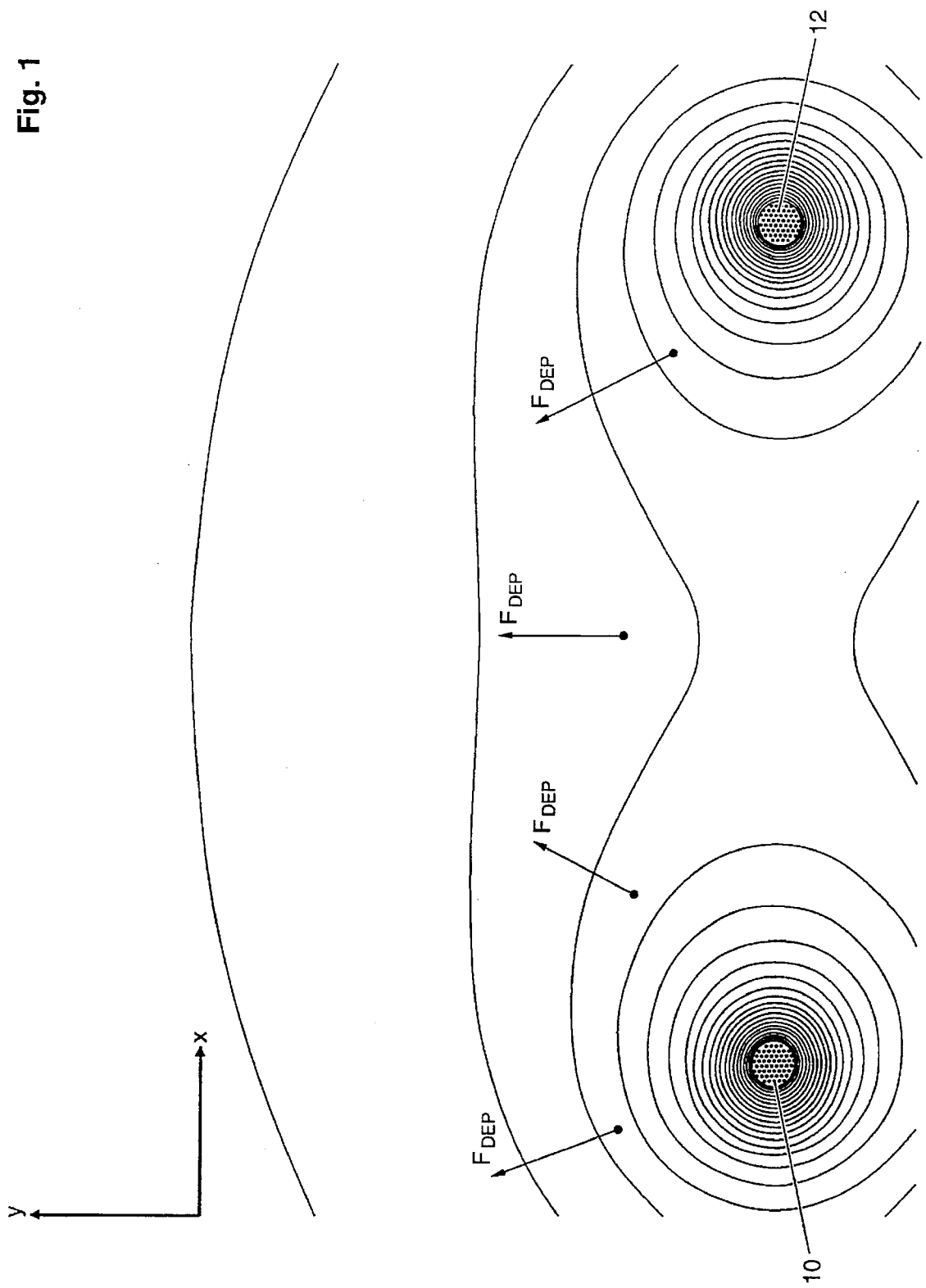
FIG. 1 is a schematic showing dielectrophoretic force produced by a nonuniform field created by the application of a potential difference to two spaced parallel electrodes on viable cells in culture medium.
Figure 2:
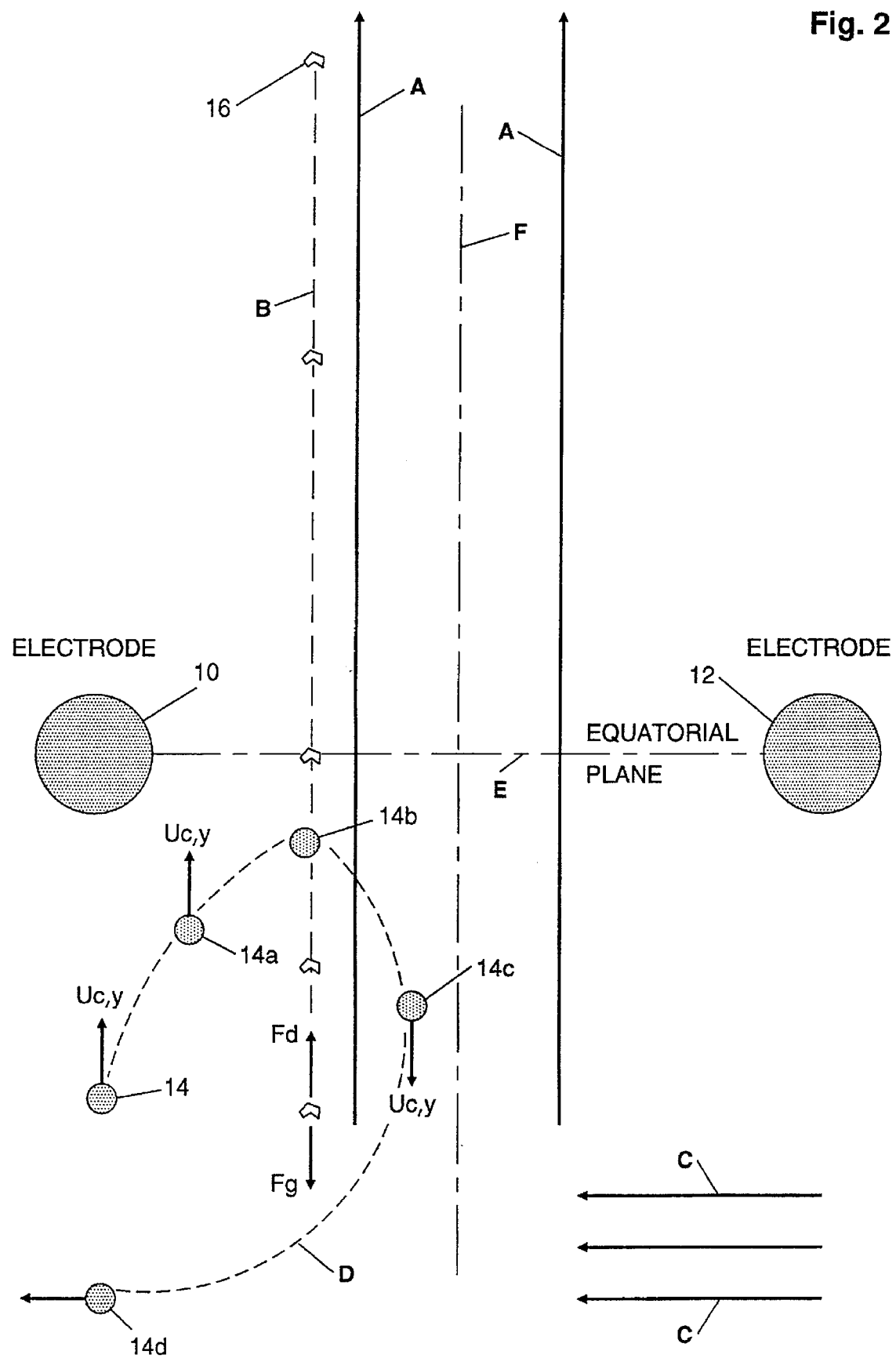
FIG. 2 is a schematic showing the effect of the dielectrophoretic force produced by the electrodes of FIG. 1 when the fluid is moved between the electrodes.
Figure 3:
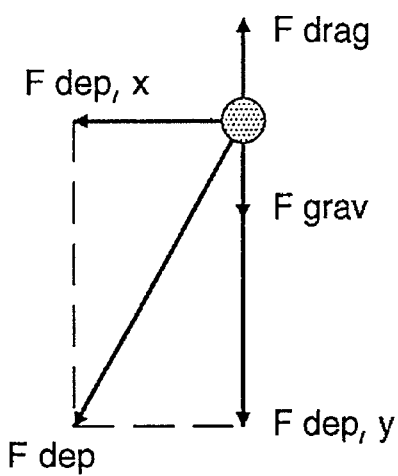
FIG. 3 is a schematic showing relationship of forces affecting the target particle.

The principle of operation of the invention can be best understood with reference to FIGS. 1–4. Electrodes 10 and 12 shown in section are spaced apart from each other with laminar fluid flow between them as indicated by the arrows A. An exemplary target particle 14, for example a viable cell, is shown being carried by the fluid. The trajectory B of an exemplary unwanted particle 16, for example cell debris, is also shown. An AC potential difference is applied to the electrodes 10, 12 to produce a negative dielectrophoretic force on the target particle 14. The electric field is shown in FIG. 1, with lines joining points of equal strength. The direction of the DEP force on a target particle 14 is shown by the arrows labelled $F_{DEP}$. $F_{DEP}$ has both x and y components and is proportional to the gradient of the square of the electric field intensity. If a series of electrodes is used, the forces increase in the y-direction and decrease in the x-direction. The y direction is in the direction of fluid flow. The y-axis DEP force should be strong enough to overcome the drag force of the fluid. If necessary, the superficial velocity of the effluent stream can be reduced by increasing the flow area of the filter. FIG. 3 shows the relationship between the drag force $F_{drag}$, the DEP force $F_{DEP}$, both x and y components and gravity $F_{grav}$. If $F_{DEP,y}$ is greater than $F_{drag}$ and opposed to it, the target particle 14 will not be carried by the flow of fluid between the electrodes 10 and 12. Instead, the target particle 14 will remain on one side of the plane E joining the electrodes 10 and 12. In case the flow of fluid between the electrodes 10 and 12 is arranged to be upward (against the pull of gravity), $F_{grav}$ can be used to assist in preventing the target particle 14 from passing between the electrodes.

Figure 4:
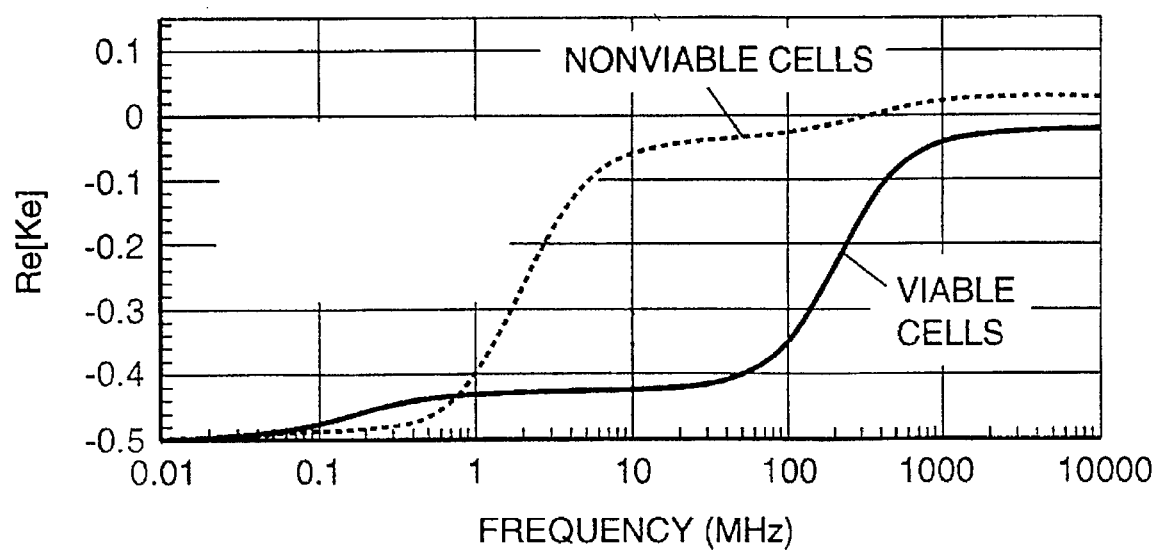
FIG. 4 is a graph showing differences in dielectrophoretic force experienced by viable and non-viable cells (note that DEP force is proportional to Re[Ke*])

As shown in FIG. 4, differential negative dielectrophoretic forces experienced by target (viable) cells and unwanted (non-viable) cells may be used to separate the viable and non-viable cells. In the region between about 1 and 100 MHz, preferably around 10 MHz, the viable cells are strongly affected by $F_{DEP}$ while the non-viable cells are much less affected. Hence, the effect of the dielectrophoretic force is to prevent the viable cells from being carried by the fluid into the conduit, while the unwanted cells are carried into the conduit.

If fluid is arranged to flow parallel to the plane of the electrodes, below the electrodes in the region where target particles 14 accumulate, as indicated by the arrow C, then the target particles 14 will tend to be swept by the flow away from the space between the electrodes 10 and 12 as indicated by the trajectory D of the target particle 14. Viable cells are thus pushed towards low field intensities, that is, towards the centerline F and away from the plane E of the electrodes.

Figure 5:
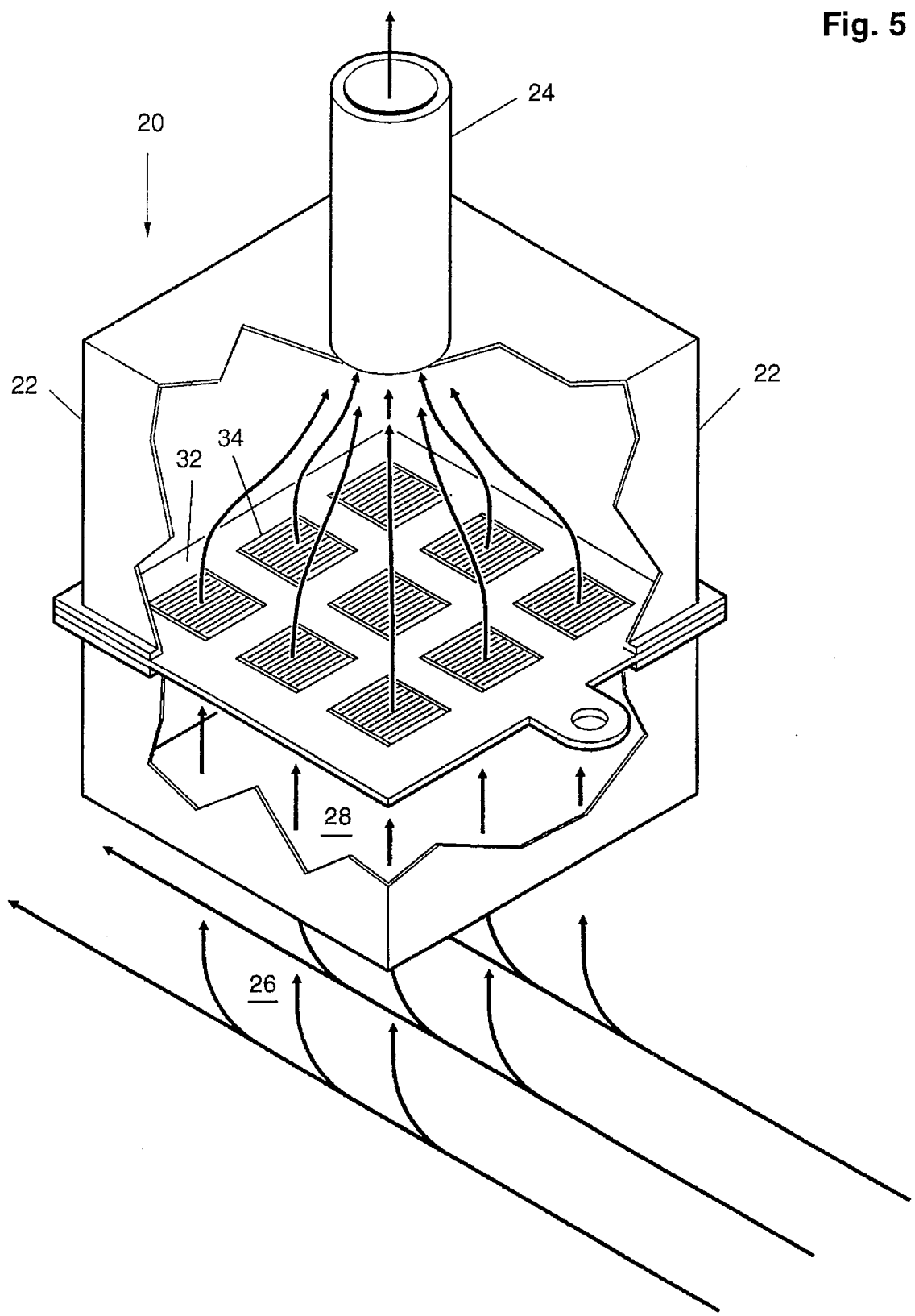
FIG. 5 is a schematic showing a filter according to the invention.
Figure 6:
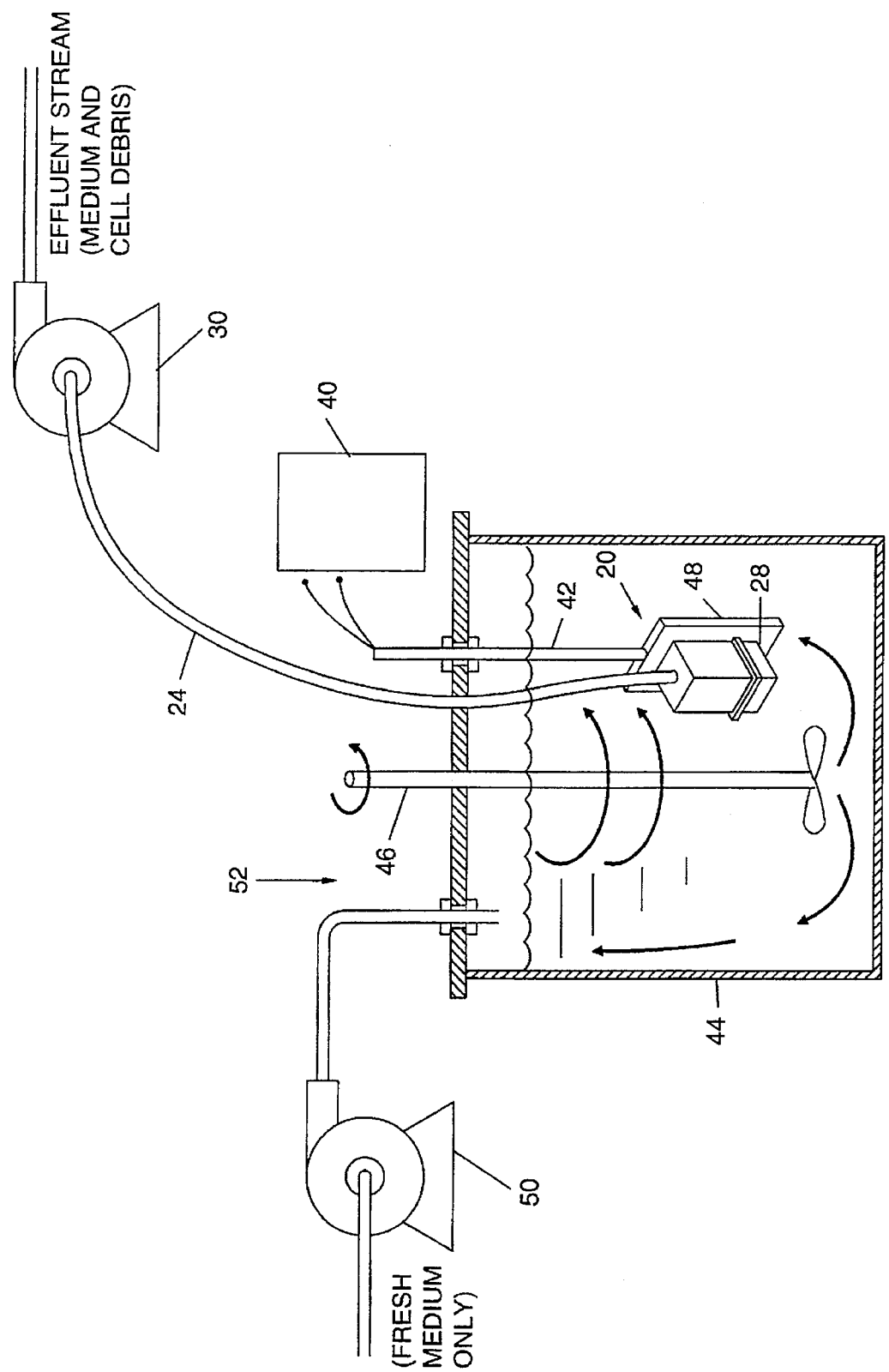
FIG. 6 is a schematic showing a filter according to the invention immersed in a bioreactor.
Figure 7:
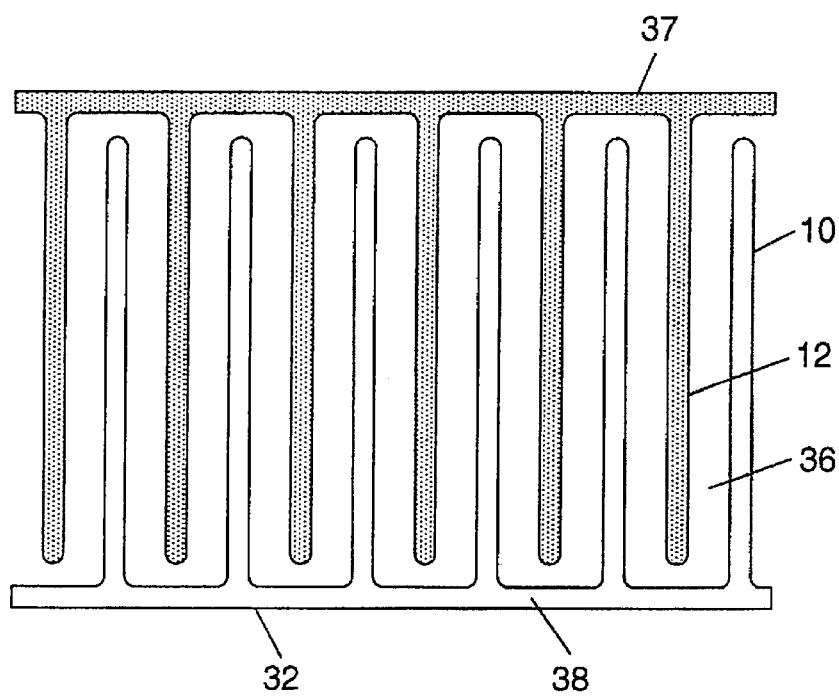
FIG. 7 is a schematic showing interdigitated electrodes for use in the filter of FIG. 5.

The spaced electrodes 10 and 12 and the field produced by them thus form straining elements of a filter. An exemplary filter 20 is shown in FIGS. 5 and 6. Encircling walls 22 and tube 24 define a conduit for the flow of fluid from region 26 to the tube 24. The walls 22 terminate in an opening 28 through which fluid from region 26 can flow into the conduit between walls 22. Pump 30, such as a peristaltic pump, connected to tube 24 pumps fluid from region 26 into the conduit through the opening 28. Across the opening 28 is located a plate 32 having, for example, nine rectangular apertures 34. Each rectangular aperture 34 has parallel interdigitated electrodes 10 and 12 extending across the aperture 34 as shown in FIG. 7. The plate 32 may be made of silicon and gold or other biocompatible metal. The interdigitated electrodes 10 and 12 create long parallel openings 36 for the flow of fluid through the plate 32. The overall dimensions of a prototype plate were 47 mm×39 mm and the thickness 200 microns. The walls 22 form a metallic housing. The electrodes 10 and 12 are created by depositing gold on a silicon substrate, with the method of metal sputtering. Gold electrode formation and the etching through the silicon for the creation of the flow channels may be based upon photolithographic techniques and silicon micromachining. The gold electrodes 10 and 12 of the prototype (an alternative option is platinum) are 8.5 mm long, 80 microns wide and about 0.45 microns thick. The distance between two consequent bars is 290 microns. The above dimensions may be varied depending on the expected operational conditions. The exerted DEP force on the cells is higher when the gap between the electrodes is further reduced in the range 60 to 120 microns and this may be a preferred operational dimension. Each aperture 34 is 11 mm×8.5 mm and includes 30 parallel electrodes 10, 12 and 29 flow channels, one between every two consequent electrode.

Electrical connections among the electrodes 10, 12 are achieved with the use of 2 gold interconnectors 37, 38. The electrodes 10, 12 are brought into contact by the interconnectors in an alternating order (i.e. the first bar in contact with the 3rd, the 5th, 7th, etc. and the 2nd bar in contact with the 4th, the 6th, 8th, etc.). This kind of connection allows one electrode to be electrically positive in an instant when the two others surrounding it are electrically negative (or the opposite). The other end of the interconnections binds to a rectangular gold pad (1.5 mm×1.0 mm) which provides sufficient contact area with the poles of a source of AC energy 40 (FIG. 6). The spaced electrodes 10, 12 and the source 40 of AC electrical energy for the electrodes form means for producing a negative dielectrophoretic force across the opening 28 into the filter 20.

The filter 20 is attached to a supporting anchor 48 that is suspended on stainless steel tubing 42 inside container 44.

The supporting anchor 48 preferably allows the filter 20 to be oriented by rotation about the axis of the tube 42 into several different positions within the container 44. A stirring device 46 rotates inside the container 44 to provide a uniform cell suspension, a portion of which flows across the opening 28 into the filter 20. Feed pump 50 supplies fresh medium to the container 44. Container 44, stirrer 46, and feed pump 50 together with other conventional elements such as oxygen supply, acid base addition, sampling ports etc (not shown) together form a bioreactor 42 which is suitable for the cultivation of animal cells under sterile conditions.

The general principle behind the operation of the filter is that of dielectrophoresis (DEP). When the poles of the electric A.C. source 40 are connected to the pads 37, 38 of the filter, a non-uniform electric field is formed in every space between and around two consequent electrodes 10, 12. The biological cells and the surrounding medium interact with this field and the result is net repulsive DEP force, which is significant for the viable cells and almost negligible for the cell debris. The intensity of the effect is subject to the applied voltage and frequency for a particular electrode geometry and cell type.

During the operation of the filter 20, the cell suspension is forced to flow through the filter channels 36. The liquid that flows through this way exerts drag forces on the cells 14 and entrains the cell debris 16. The viable cells 14 are not passing through since the DEP force, higher in magnitude than the drag force, pushes these cells continuously away from the filtration area. The effect becomes even stronger when the cells form aggregates, by further interacting with themselves, due to the polarization effects under the imposed electric field. These cell complexes increase the separation efficiency, since the DEP force is proportional to the volume of the particle. Therefore, the higher the cell density, the better the retention becomes. This relationship is an added advantage of the disclosed DEP filter since the separation efficiency of all the other devices decreases with increasing cell density.

In general, fluid is pumped into a conduit, such as defined by the walls 22 of filter 20, through an opening 28 in the conduit. A negative dielectrophoretic force is applied to target particles at the opening, the negative dielectrophoretic force having sufficient strength to prevent the target particles from entering the conduit. When operated in a bioreactor with fluid flow in the bioreactor that includes a component of flow parallel to the opening, viable cells are swept back into the main body of the bioreactor and thus concentrated.

EXAMPLES

Frequency range experiment: FIG. 4 shows a typical DEP frequency spectrum for viable (symbol 14) and non-viable cells (symbol 16). The DEP effect is strongly related to the applied field frequency. For a certain band of frequencies, the resulting DEP force can be very strong for the viable cells and negligible for the non-viable ones. This frequency range varies with the cell type. For cells inside their growth medium dielectrophoresis can be only negative. The vertical axis in FIG. 4, Re[Ke], is directly proportional to the DEP force, and is the term which relates the dielectrophoretic effect to the applied frequency. The figure shows clearly that, as the frequency goes higher, the force can remain strong for the viable cells while turns negligible for the non-viable. The numerical values Re[Ke] can take vary from 0.0 to −0.5 for negative DEP. Working within this range of frequencies and taking into account the effect of the size difference ($F_{DEP} \sim r_c^3$), one can expect a force two orders of magnitude or higher for the viable cells.

Effect of the applied A.C. frequency on the viable cell retention

Figure 8:
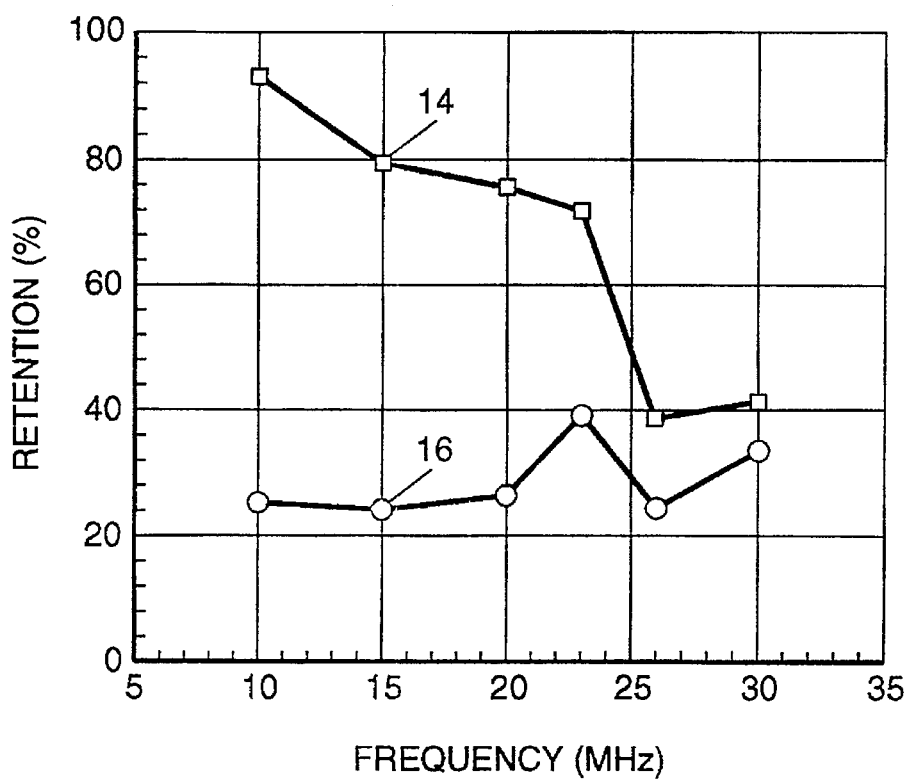
FIG. 8 is a graph showing the effect of frequency on cell retention.

FIG. 8 presents the results from experiments regarding the role of frequency in viable cell separation. These results clearly verify the theoretical predictions. High degree of viable cell retention is achievable if the operating frequency range is within the suggested limits (see FIG. 4). The corresponding retention of non-viable cells is very low.

Effect of the applied voltage on viable cell retention

Figure 9:
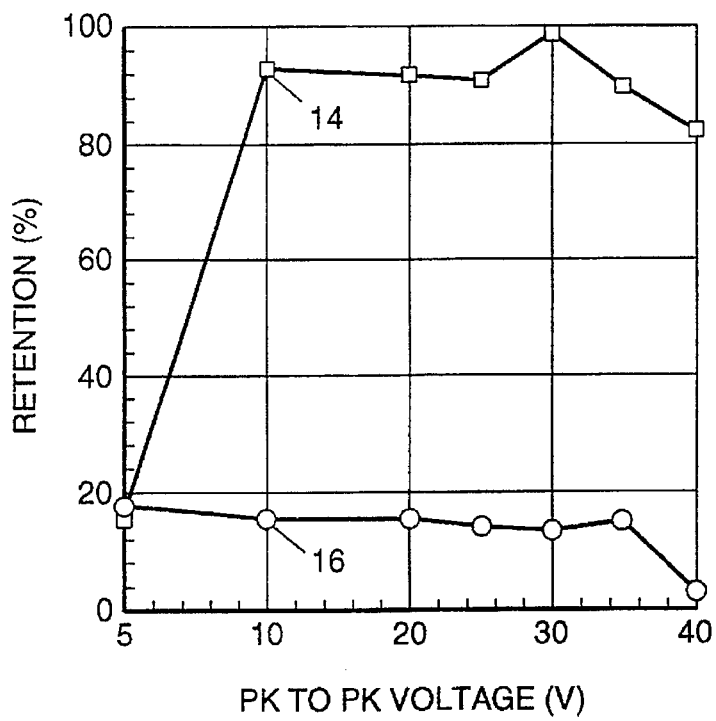
FIG. 9 is a graph showing the effect of voltage on cell retention.

FIG. 9 shows that the increment on the applied voltage facilitates the cell separation. That was expected since the DEP force is directly proportional to the voltage squared.

Effect of the medium replenishment rate on viable cell retention

Figure 10:
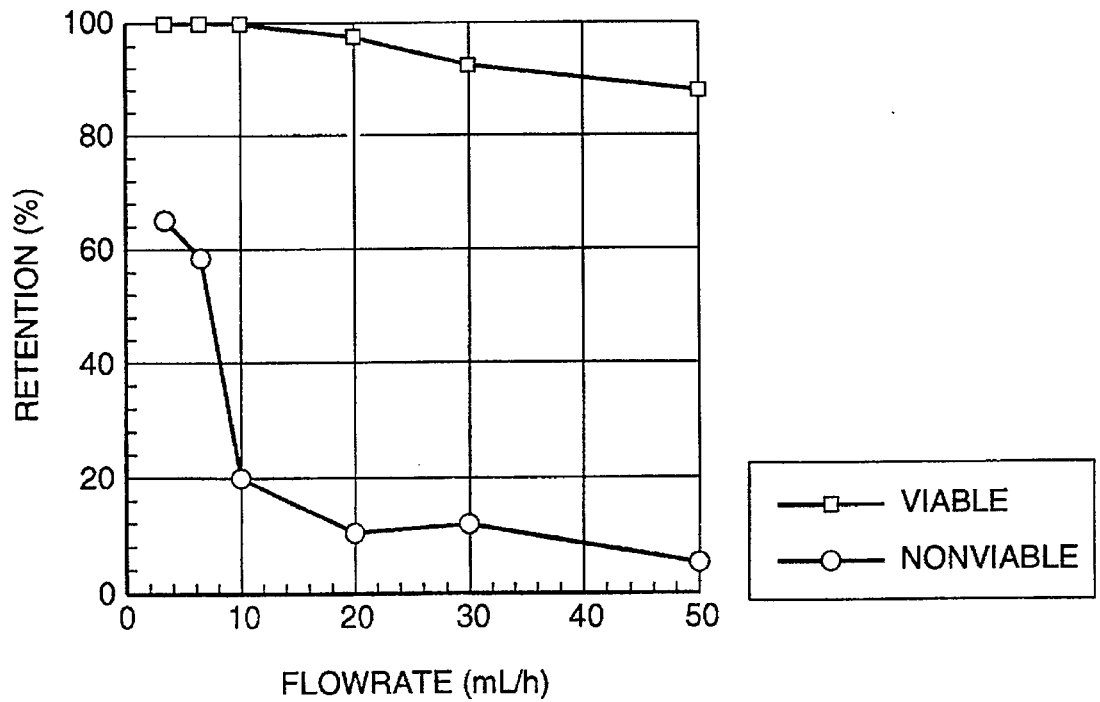
FIG. 10 is a graph showing effect of flow rate on cell retention.

FIG. 10 shows that the increment of the flowrate of the effluent stream reduces the filter capabilities. As the velocity of the out flowing stream becomes higher, the drag forces acting on the cells become higher too. Therefore, the net force decreases. The effect is beneficial in regards of the debris removal. This set of results indicates that an overall optimization of parameters like voltage, frequency and filter characteristic dimensions is required for achieving good results at high flowrates.

The above described invention has numerous advantages:

(a) Continuous operation: The absence of moving parts or flow-channels susceptible to clogging guarantees the uninterrupted operation of the filter.

(b) Effective cell separation: The negative DEP force is strong for the viable cells, (within a band of electric A.C. field frequencies) and overcomes the net force which is pushing the cells towards the exit of the bioreactor. Therefore, the viable cells are retained inside the bioreactor.

(c) Selective separation of viable cells: For the same A.C. frequencies the force acting on the non-viable cells is very weak. This makes the non-viable cells to be entrained by the out flowing medium, and gives very high degree of selectivity in the separation. The investigation and detection of this band of field frequencies is possible for all kinds of cells and can be obtained with available experimental methods and devices in Kaler, K. V. I. S., Xie, J-P, Jones, T. B., Paul, R., 1992. "Dual-frequency dielectrophoretic levitation of Canola protoplasts". Biophys. J. 63: 58–69.

(d) No Decelerating effects on cell growth and productivity rates: This is possible since there are neither shear stresses, as in filtration, nor external separation loops or dilutions, that keep the cells outside of their growth environment for long times. The filtering device is the first one that can be internally installed and handled as a part of the bioreactor. In addition to that, the cell interactions with the electric field are kept minimal, if the mixing pattern inside the bioreactor (eg. one available from CelliGen) is such that the circulating stream that is created pushes the cells away from the field and towards the main cell suspension.

(e) Low energy consumption: The system preferably operates at very high frequencies (in the vicinity of 10 MHz or higher), where the current flow is minimal. Consequently, the Joule effect (or heating effect) will be low as well. In addition, the range of the applied peak-to-peak voltage is relatively low (in the range 5 to 30 volts). In other words, an effective DEP field can be created without the requirement of a significant energy input.

(f) Compact design and simplicity in operation: Once the device is put inside the bioreactor and the A.C. field is set on, no other interventions are required. The structure of the filter can be kept very simple (even one part) and the filter can be readily mounted inside the bioreactor.

(g) Scale-up capabilities: All that is needed for an operation in a large scale is the increment of the filtration area, in order for larger fluid volumes to be accommodated.

The actual DEP-filter can be manufactured and implemented in many different ways both in terms of electrode configuration and in terms of housing device design, some of which will likely have better retention efficiencies than those reported for the prototype. Furthermore, a multi stage configuration of filter plates 32 may be implemented with much superior results whereby each filter plate 32 is subjected to a slightly different A.C. field.

A person skilled in the art could make immaterial modifications to the invention described and claimed in this patent without departing from the essence of the invention.

The embodiments of the invention in which an exclusive property or privilege is claimed are defined as follows:

1. A filter comprising:
   a conduit having an opening for flow of fluid into the conduit;
   a pump for pumping fluid into the conduit through the opening;
   electrodes spaced apart from each other across the opening such that fluid flowing through the opening passes between the electrodes;
   means for providing electrical energy having a frequency and voltage applied to the electrodes, wherein the electrical energy is adapted to create an electric field between the electrodes comprising a negative dielectrophoretic force with a component opposed to the flow of target particles carried by the fluid flow through the opening and the component has sufficient strength to exceed drag forces acting on the target particles and prevent the target particles from passing between the electrodes into the conduit; and
   means to sweep target particles away from the opening.

2. The filter of claim 1 in which there are plural pairs of parallel interdigitated electrodes extending across the opening.

3. The filter of claim 2 further in combination with a bioreactor, the filter being mounted in the bioreactor.

4. The filter of claim 3 in which the target particles are viable cells and the fluid is a culture medium.

5. The filter of claim 4 in which the source of electrical energy produces an electrical field with a frequency of about 10 MHz or higher.

6. The filter of claim 5 in which the means for providing electrical energy is adapted to produce an electrical field with a frequency of about 10 MHz or higher.

7. The filter of claim 1 in which the means for providing electrical energy is adapted to produce an electric field that leaves unwanted particles substantially unaffected by the negative dielectrophoretic force, such that target particles may be separated from unwanted particles.

8. The filter of claim 1 in which the conduit is oriented such that the direction of fluid flow into the conduit is opposed to the pull of gravity.

9. A bioreactor comprising:
   a container for fluid, the container being suitable for the cultivation of animal cells under sterile conditions;
   a conduit extending from within the container to outside the container, the conduit having an opening for flow of fluid into the conduit;
   means in the container for stirring the fluid and provide a flow of fluid with a component of flow parallel to the opening to sweep material away from the opening;
   a pump for pumping fluid into the conduit through the opening; and
   means for producing a negative dielectrophoretic force on target particles carried by the fluid, wherein the negative dielectrophoretic force is adapted to have a component opposed to the flow of fluid and the component of the negative dielectrophoretic force has sufficient strength to prevent the target particles from passing into the conduit.

10. The bioreactor of claim 9 in which the means for producing a negative dielectrophoretic force comprises:
    electrodes spaced apart from each other across the opening such that fluid flowing through the opening passes between the electrodes; and
    a source of electrical energy for the electrodes.

11. The bioreactor of claim 10 in which the source of electrical energy has output capable of producing an electric field that leaves unwanted particles substantially unaffected by the negative dielectrophoretic force, such that target particles may be separated from unwanted particles.

12. The bioreactor of claim 11 in which the target particles are viable cells, the fluid is a culture medium and the unwanted particles are selected from the group comprising non-viable cells and cell debris.

13. The bioreactor of claim 12 in which there are plural pairs of parallel interdigitated electrodes extending across the opening.

14. The bioreactor of claim 13 in which the source of electrical energy produces an electric field with a frequency in the vicinity of 10 MHz or higher.

15. The bioreactor of claim 9 in which the conduit is oriented in normal operation such that direction of fluid flow into the conduit is opposed to the pull of gravity.

16. The bioreactor of claim 9 in which the the negative dielectrophoretic force has sufficient strength to exceed drag forces acting on the target particles.

17. A method for filtering target particles from a fluid contained in a bioreactor, the method comprising the steps of:
    pumping fluid from the container into a conduit through an opening in the conduit;
    moving fluid in the container in a direction that includes a component of flow parallel to the opening to sweep material away from the opening; and
    applying a negative dielectrophoretic force to target particles at the opening, the negative dielectrophoretic force having sufficient strength to prevent the target particles from entering the conduit.

18. The method of claim 17 in which the conduit is oriented such that direction of fluid flow into the conduit is opposed to the pull of gravity.

19. The method of claim 17 in which
    the negative dielectrophoretic force has sufficient strength to exceed drag forces acting on the target particles.

20. The method of claim 17, in which the negative dielectrophoretic force is applied by a source of electrical energy connected to plural pairs of interdigitated electrodes located across the opening.

21. The method of claim 20 in which the frequency of the output of the source of the electrical energy is about 10 MHz or higher.

22. The method of claim 21 in which the voltage of the electrical energy is at least 5 volts peak to peak.

23. The method of claim 20 in which the flow rate of fluid is at least 5 mL per hour.

24. The method of claim 17 in which the negative dielectrophoretic force is created by an electrical source applied to plural pairs of electrodes located across the opening and further including:

creating the dielectrophoretic force with an electric field that leaves unaffected unwanted particles carried by the fluid.

* * * * *